United States Patent [19]

Giovannella et al.

[11] Patent Number: 5,225,404
[45] Date of Patent: Jul. 6, 1993

[54] METHODS OF TREATING COLON TUMORS WITH TUMOR-INHIBITING CAMPTOTHECIN COMPOUNDS

[75] Inventors: Beppino C. Giovannella, Houston, Tex.; Leroy F. Liu, Lutherville, Md.; Milan Potmesil, New York, N.Y.; Monroe C. Wall, Chapel Hill, N.C.; Robert F. Silber, New York, N.Y.; Mansukh C. Wani, Durham, N.C.

[73] Assignee: New York University, New York, N.Y.

[21] Appl. No.: 432,066

[22] Filed: Nov. 6, 1989

[51] Int. Cl.$^5$ ............... A01N 57/00; A61K 31/685
[52] U.S. Cl. ............................... 514/81; 514/283
[58] Field of Search ............................. 514/81, 283

[56] References Cited

U.S. PATENT DOCUMENTS

| Re. 32,518 | 10/1987 | Miyasaka et al. | 546/48 |
|---|---|---|---|
| 3,894,029 | 7/1974 | Winterfeldt et al. | 546/48 |
| 4,031,098 | 6/1977 | Sugasawa et al. | 546/48 |
| 4,399,276 | 8/1983 | Miyasaka et al. | 542/416 |
| 4,399,282 | 8/1983 | Miyasaka et al. | 546/48 |
| 4,473,692 | 9/1984 | Miyasaka et al. | 546/48 |
| 4,513,138 | 4/1985 | Miyasaka et al. | 546/48 |
| 4,545,880 | 10/1985 | Miyasaka et al. | 204/158 R |
| 4,604,463 | 8/1986 | Miyasaka et al. | 544/125 |
| 4,774,236 | 9/1988 | Cook et al. | 514/176 |
| 4,894,456 | 1/1990 | Wall et al. | 546/41 |
| 4,914,205 | 4/1990 | Sawada et al. | 546/70 |
| 4,981,968 | 1/1991 | Wall et al. | 544/361 |
| 5,049,668 | 9/1991 | Wall et al. | 544/361 |
| 5,053,512 | 10/1991 | Wani et al. | 546/48 |
| 5,106,742 | 4/1992 | Wall et al. | 435/233 |

FOREIGN PATENT DOCUMENTS

| 0074256 | 3/1983 | European Pat. Off. . |
| 0220601 | 5/1987 | European Pat. Off. . |
| 61-50985 | 3/1983 | Japan . |
| 59-5188 | 1/1984 | Japan . |
| 59-51287 | 3/1984 | Japan . |
| 59-51289 | 3/1984 | Japan . |
| 59-501288 | 3/1984 | Japan . |
| 61-85319 | 4/1986 | Japan . |
| 61-85389 | 4/1986 | Japan . |

OTHER PUBLICATIONS

Gottlieb, J. A. et al., Cancer Chemo. Rep. 54:461–470, 1970.
Jaxel, C. et al. Cancer Res. 49:1465–1469, 1989.
Potmesil, M. et al., Cancer Res. 48:3537–3543, 1988.
Wani, M. C. et al., J. Med. Chem. 23:554–560, 1980.
Leibovitz, A. et al., Cancer Res. 36:4562–4569, 1976.
Fogh, J. et al., In "Human Tumor Cells In Vitro", Fogh, J. ed., Plenum Press, New York, 1975. pp. 115–141.
Liu, L. F. et al., Proc. Natl. Acad. Sci. USA 78:3487–3491, 1981.
Muggla, F. M. et al., Cancer Chemo Rep. 56:515–521, 1972.
Wall, M. E. et al., J. Med. Chem. 29:1553–1555, 1986.
Nelson, W. G. et al., Cancer Res. 47:3246–3250, 1987.
Hisang, Y.-H. et al., Cancer Res. 49:4386–4389, 1989.
Wani, M. C. et al., J. Med. Chem. 30:2317–2319, 1987.
Giovanella, B. C. et al., Cancer 52:1146–1152, 1983.
Wani, M. C. et al., J. Med. Chem. 30:1774–1779, 1987.
Hsiang, Y.-H. et al., Cancer Res. 48:1722–1726, 1988.
Wani, M. C. et al., J. Med. Chem. 30:1774–1779, 1987.
Wani, M. C. et al., J. Med. Chem. 29:2358–2363, 1986.
Hsiang, Y.-H. et al., J. Biol. Chem. 97:14873–14878, 1985.

(List continued on next page.)

*Primary Examiner*—Nathan M. Nutter
*Attorney, Agent, or Firm*—Darby & Darby

[57] ABSTRACT

The present invention provides methods of treating malignant colon and colo-rectal cancer in mammals, by reducing or inhibiting or retarding such colon cancer tumors in mammals. These methods employ the administration of a tumor-inhibiting or reducing camptothecin compound, e.g., 9-amino-20(RS)-camptothecin, 10,11-methylenedioxy-20(RS)-camptothecin, and the sodium salt of 10,11-methylenedioxy-20(RS)-camptothecin, or a combination thereof. Also provided are pharmaceutical formulations.

31 Claims, 5 Drawing Sheets

OTHER PUBLICATIONS

Hsiang, Y.-H. et al., abstract 683 from The American Association for Cancer Research, vol. 29, Mar., 1988.

*Chemical Abstracts*, vol. 106(25), Abstract No. 207285z (1987).

*Chemical Abstracts*, vol. 106(15), Abstract No. 120133z (1987).

*Chemical Abstracts*, vol. 106(15), Abstract No. 11479a (1987).

*Chemical Abstracts*, vol. 106(13), Abstract No. 95753s (1987).

*Chemical Abstracts*, vol. 103(9), Abstract No. 64374c (1985).

*Chemical Abstracts*, vol. 101, Abstract No. 136077r (1984).

*Chemical Abstracts*, vol. 101(11), Abstract No. 91322Z (1982).

*Chemical Abstracts*, vol. 101(10), Abstract No. 78770z (1984).

*Chemical Abstracts*, vol. 100(21), Abstract No. 167724j (1983).

*Chemical Abstracts*, vol. 100, Abstract No. 139434W (1984).

*Chemical Abstracts*, vol. 97, Abstract No. 188278b (1982).

*Chemical Abstracts*, vol. 96(9), Abstract No. 69271p (1981).

*Chemical Abstract*, vol. 95(15), Abstract No. 133209h (1981).

*Chemical Abstracts*, vol. 94(12), Abstract No. 90169e (1980).

*Chemical Abstracts*, vol. 94(1), Abstract No. 4143n (1980).

*Chemical Abstracts*, vol. 92(5), Abstract No. 37766e (1980).

*Chemical Abstracts*, vol. 92(3), Abstract No. 18799b (1980).

*Chemical Abstracts*, vol. 90(4), Abstract No. 28930K (1979).

*Chemical Abstracts*, vol. 90(3), Abstract No. 22857v (1979).

*Chemical Abstracts*, vol. 84, Abstract No. 115629p (1976).

*Derwent* 87-179979/25.

Nicholas et al., (1990), *Journal of Medicinal Chemistry*, vol. 33, No. 3, pp. 972–978.

Ohro et al., (1989), *Proc. Annu. Meet. Am. Soc. Clin. Oncol.*, 8:A1019.

Hertzberg et al., (1989), *J. Med. Chem.*, vol. 32(3), pp. 715–720.

Giovanella et al., (1989) *Science*, vol. 246, pp. 1046–1048.

Hsiang et al., (1989), *Proc. Annu. Meet. Am. Assoc. Cancer Res.*, 30:A2476.

Hertzberg et al., (1989), *Proc. Annu. Meet. Am. Assoc. Cancer Res.*, 30:A2485.

Pommier et al., (1988), *Proc. annu. Meet. Am. Assoc. Cancer Res.*, 29:A1080.

Lin et al., (1988), *Yao Hsueh Hsueh Pao*, vol. 23(3) pp. 186–188.

Ronman et al. (1981), *Journal of Labelled Compounds and Radiopharmaceuticals*, vol. 18(3), pp. 319–329.

Danishefsky et al., (1974), *J. Org. Chem.*, vol. 39(28), pp. 3430–3432.

Plattner et al., (1974), *J. Org Chem.*, vol. 39(3), pp. 303–311.

Plattner, et al., (1972), *J. Amer. Chem. Soc.*, vol. 94(24), pp. 8615–8616.

Govindachari et al., "9-Methoxycampthecin A new Alkaloid from *Mappia foetida* Miers", pp. 453–454.

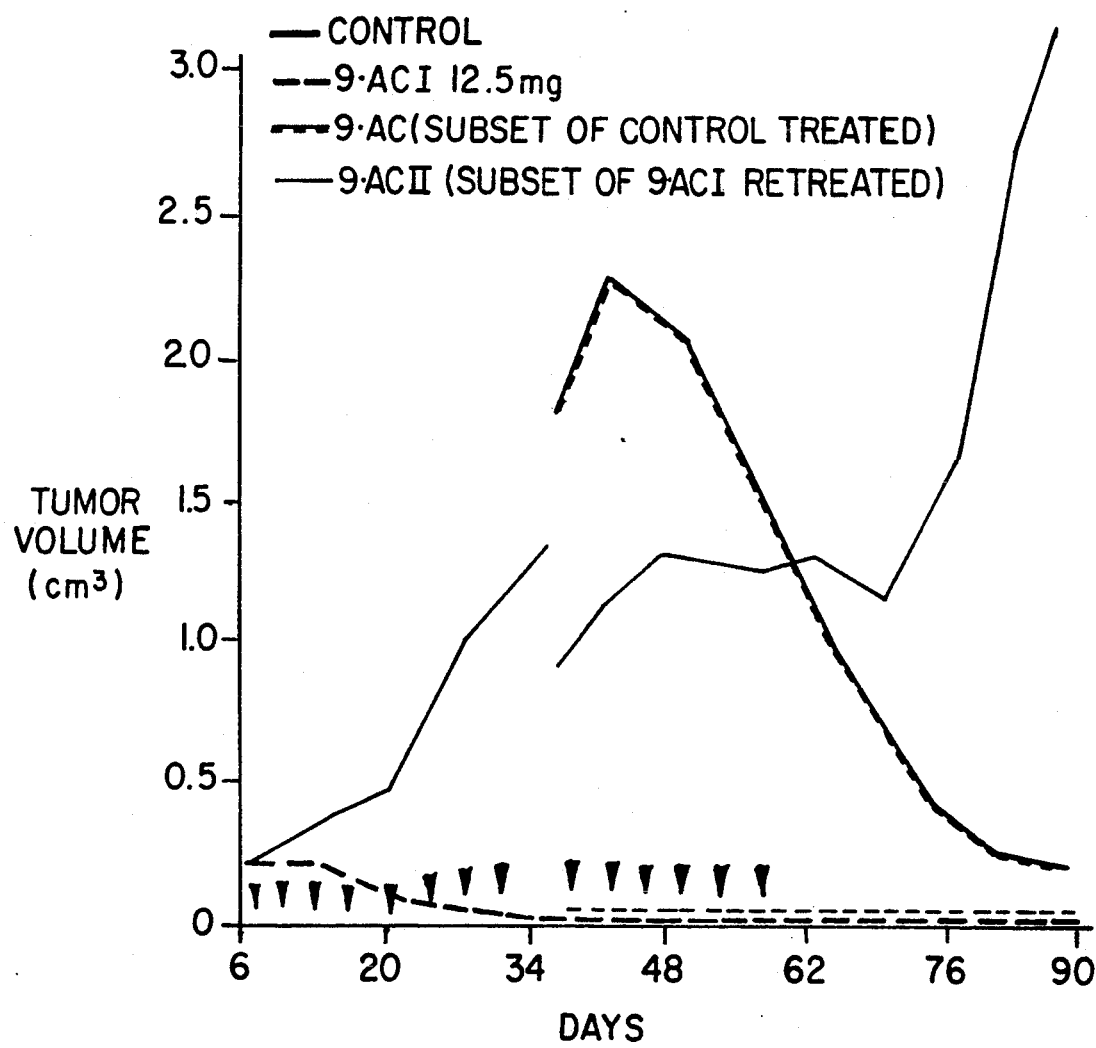

METHODS OF TREATING COLON TUMORS WITH TUMOR-INHIBITING CAMPTOTHECIN COMPOUNDS

The government has rights to this invention by virtue of funding under Grant No. RO1CA 38996-04 from the National Cancer Institute.

This invention relates to methods for treating colon cancer in mammals. More particularly, the invention relates to methods for treating malignant colon tumors and colo-rectal tumors in mammals by administering an effective amount of a tumor-inhibiting camptothecin compound, and consequently reducing the volume size of such tumors. Such a tumor-inhibiting camptothecin compound includes at least one member of a group of tumor-reducing camptothecin compounds including 9-amino-20(RS)-camptothecin, 10,11-methylenedioxy-20(RS)-camptothecin; and the sodium salt of 10,11-methylenedioxy-20(RS)-camptothecin.

BACKGROUND OF THE INVENTION

Colon cancer, which includes colorectal adenocarcinoma, primary or metastatic adenocarcinoma, and the like, is a major health concern today in terms of disease incidence. It has been estimated that one out of twenty-five Americans will develop some form of colon cancer during the course of his lifetime. Sugarbaker, P. H. et al., in *Cancer*, DeVita, V. T., et al. (Eds.), Lippincott Publ. Philadelphia, pp. 795–884 (1985).

In terms of treatment, surgery has been widely used with good, mixed or less than favorable results. Particularly among colon cancer patients with locally advanced or metastatic disease, the prognosis is extremely unfavorable with a high rate of morbidity and mortality.

Drug therapies have been tried with less than favorable results. The anti-neoplastic compound, 5-fluorouracil (5-FU), has been the major drug of choice in treating colon cancer, and its use has proven to be only marginally effective. 5-FU may reduce colon tumor size temporarily but there has been little evidence to show that the survival times of patients have been substantially prolonged or that "cures" are obtained (based on five year periods of remission). Chemotherapy with 5-FU has been used in patients with metastases to the liver, but temporary improvement is observed in only 25 percent or less of such cases, and the overall, survival is not significantly affected. LaMont, J. T. and Isselbacher, K. J., in *Harrison's Principles of Internal Medicine* (10th ed.) McGraw-Hill, New York, p. 1764, (1983). Despite the marginal effectiveness of 5-FU no other drugs or combination therapy has been convincingly shown to be more effective. Sugarbaker P. H. et al., supra. Woolley, P. V., et al., *New Eng. J. Med.*, 312:1465 (1985).

Drug therapies have also been evaluated with respect to treating human cancer, e.g., human colon cancer xenograft lines, in which human tumors are serially heterotransplanted into immunodeficient, so called "nude" mice, and the mice then tested for their responsiveness to a specific drug. Giovanella, B. C., et al., *Cancer* 52(7):1146 (1983). The data obtained in these studies strongly support the validity of heterotransplanted human tumors, including colon tumors, into immunodeficient mammals, such as "nude" mice, as a predictive model for testing the effectiveness of anticancer agents.

The sodium salt of a naturally occurring alkaloid, camptothecin, was used in a brief clinical trial to evaluate toxic effects on patients with advanced incurable cancers. Gottlieb, G. A., et al., *Cancer Chemotherapy Rep.* 54:461 (1970). Few conclusions could be drawn from this study, although median survival for those patients responding to the treatment increased from about two months to about 3.5+ months.

Camptothecin derivatives or analogs have been synthesized and employed as antileukemic agents in mice (see e.g., Wani, M. C., et al., *J. Med. Chem.* 23:544, 1980; Wani, M. C., et al., *J. Med. Chem.* 30:1774 (1987); and Wani, M. C. et al., *J. Med. Chem.* 30:2317 (1987).

In U.S. Pat. Nos. 4,473,692 and 4,545,880, Miyasaka et al. disclose 10-substituted camptothecin derivatives and processes for their preparation. The 10-substituted camptothecin derivatives are said to possess anti-tumor activity with reduced or slight toxicity in comparison to the parent camptothecin compound. Miyasaka et al. do not disclose specific tumor targets nor do they indicate what level of reduced or slight toxicity is achieved by using their 10-substituted camptothecin compounds.

Recently, the enzyme, human topoisomerase I, has been examined in various human cancers, e.g., leukemia, lymphoma. Potmesil M. et al., *Cancer Res.* 48:3537 (1988). Human topoisomerase I is known to be a monomeric protein with an apparent molecular weight of 100,000 daltons. The swivel-like function of the enzyme has been implicated in various DNA transactions (replication, transcription and recombination). Purified mammalian topoisomerase I relaxes positively-supercoiled as well as negatively-supercoiled DNA in a mechanism which involves the transient breakage of one of the two DNA strands and the formation of a covalent topoisomerase I-DNA complex. In this complex, the enzyme is covalently linked to the 3'-phosphoryl end of the broken DNA backbone.

Recently, it was disclosed that topoisomerase I enzyme levels were on average higher in cancerous tissue, e.g., surgical specimens of colorectal carcinoma, in comparison to the enzyme level in normal mucosa (Hsiang, Y.-H., et al., *Proc Ann Meet. of the Amer. Assoc. Cancer Res.* 29:172 (1988) Abstract. Although it was stated that topoisomerase I could be considered as an alternative target in chemotherapy of this [colorectal carcinoma] disease, no disclosure or suggestion at all was made as to any specific topoisomerase I interacting drugs.

In view of very poor 5-year survival rates (approximately 50 percent or less) for patients undergoing conventional treatment for colonic cancer, e.g., surgical resection, or chemotherapy with 5-FU, it would be extremely useful to discover a new way to effectively treat human malignant colon tumors using drugs or compounds, following surgery, for example, which helps to establish the diagnosis and removes the bulk of cancer. The drug treatment would also be helpful for patients with advanced disease which has metastasized or spread to various organs, so that surgery is not feasible to remove all the cancerous tissues.

SUMMARY OF THE INVENTION

It has now been discovered that malignant colon tumors and colo-rectal tumors in mammals can be retarded and treated effectively through administration to the mammal in need of such treatment of an effective amount for treating said tumors of a tumor-inhibiting camptothecin compound.

It has also been discovered that the volume size of human malignant colon tumors and colo-rectal tumors can be reduced by administrating an effective amount of a colon-tumor reducing camptothecin compound which will also inhibit DNA topoisomerase I activity so as to reduce the volume size of such tumors, eradicate the tumor entirely and "cure" the mammal.

BRIEF DESCRIPTION OF THE FIGURES

FIG. 5 shows the results of the treatment obtained in another poorly differentiated human colon cancer cell line designated SW48, which is extremely unresponsive to any kind of treatment following the first and second courses of treatment using 9-amino-20(RS)-camptothecin.

DETAILED DESCRIPTION OF THE INVENTION

Figure 1:
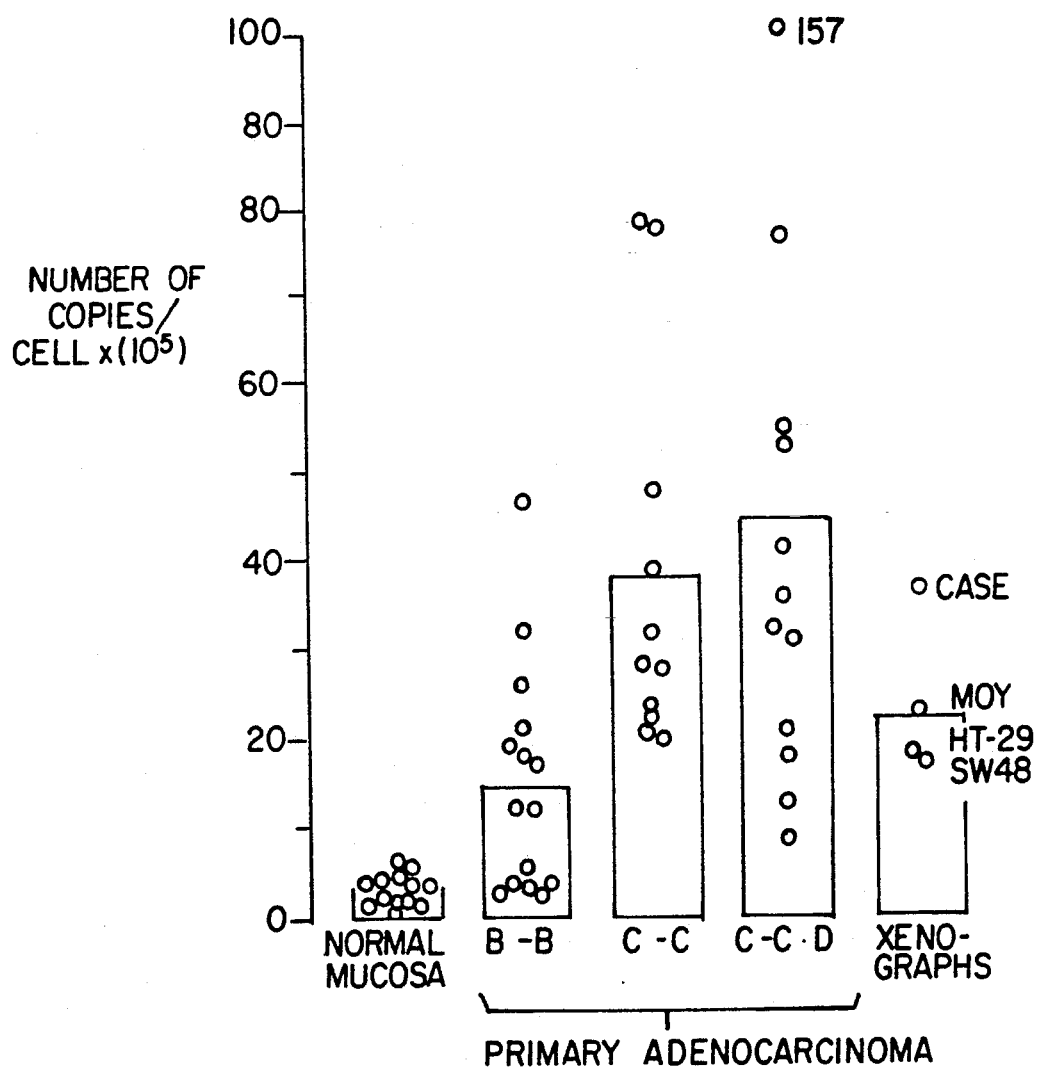
FIG. 1 illustrates the level of DNA topoisomerase I in various human colon cancer specimens.

All publications, patents and patent applications cited in this specification are hereby incorporated by reference in their entirety.

20(S)-camptothecin is a plant alkaloid isolated from *Camptotheca acuminata*. This substance has been shown to be effective against mouse leukemias. Chemical derivatives of 20(S)-camptothecin can be prepared either in a semisynthetic or totally synthetic way. See e.g., the three Wani, M. C., et al references: (1980), (1987) and (1987), supra. The sodium salt of 20(S)-camptothecin was tested in clinical trials in patients with various cancers, unresponsive to previous treatments. In several patients, some of them with colorectal cancer, a temporary relief of the disease was noted, accompanied by a marginal prolongation of median survival (Gottlieb G. A. et al., *Cancer Chemoth. Rep.* 54:461 (1970); Muggia F. M. et al. *Cancer Chemoth. Rep.* 56:515, 1972). Leukopenia became a limiting factor, however, preventing more intensive treatment of the patients. Hemorrhagic cystitis was the most prominent non-hematological complication.

The present invention provides a method of treating malignant colon tumors or colo-rectal tumors in mammals through administration of an effective anti-tumor amount for treating said tumors of specific camptothecin derivatives for inhibiting growth of malignant colonic tumors. These derivatives are also DNA topoisomerase I-inhibitors and are members selected from a larger group of compounds, and these consist of 9-amino-20(RS)-camptothecin, 10,11-methylenedioxy-20(RS)-camptothecin, and the sodium salt of 10,11-methylenedioxy-20(RS)-camptothecin, or a combination of any of the foregoing. The amount of the compound administered to the mammal is essentially the same amount that is effective to inhibit topoisomerase I enzymatic activity.

The S form with pure stereochemistry may also be employed according to this invention and has been determined to be in fact approximately two fold more potent than the mixtures of the pure and racemic (RS) forms. The existence of the (RS) mixture is inherent in the synthesis of the drugs, and the drugs are more conveniently prepared in this way. However, further chemical steps may be employed in order to prepare a pure (S) preparation.

As used herein, the term "malignant colon tumor" is intended to encompass all forms of human colon carcinoma and malignant tumors which occur in the large bowel or large intestine, including colo-rectal cancer, adenocarcinoma, primary adenocarcinoma, metastatic adenocarcinoma, as well as poorly differentiated, moderately differentiated, and well differentiated forms.

The three colon tumor-inhibiting or tumor-reducing camptothecin compounds employed in the method of the present invention may be prepared using techniques and procedures which were established and invented by co-inventor(s) of the present invention. The techniques and procedures are known in the art.

9-amino-20(RS)-camptothecin may be prepared by following the method described in Wani M. C., et al., *J. Med. Chem.* 23:544 (1980); Wani, M. C., et al., *J. Med. Chem.* 30:1773 (1987) and Wani, M. C., et al., *J. Med. Chem.* 30:2317 (1987).

10,11-methylenedioxy-20(RS)-camptothecin is prepared using processes well-known in the art. Wani et al. (1987) and (1987) ibid. describe a method for the preparation of 10,11-methylenedioxy-20(RS)-camptothecin.

The sodium salt of 10,11-methylenedioxy-20(RS)-camptothecin is prepared using techniques well-known to those skilled in the art. As one example, the sodium salt of this compound may be prepared following the method described by Wani, M. C., et al. *J. Med. Chem.*, (1987) and (1987) ibid.

In addition, methods for the synthesis of camptothecin compounds are described in Monroe E. Wall et al., U.S. patent application Ser. No. 032,449, filed Mar. 31, 1988, now U.S. Pat. No. 4,894,456; and in Monroe E. Wall et al., U.S. patent application Ser. No. 250,094, filed Sep. 28, 1988, now U.S. Pat. No. 4,981,968, which is a continuation-in-part of the '339 application.

Prior to administering these camptothecin compounds to mammals, it is important to purify the subject compound to homogeneity, as is required by FDA regulations for any drug or compound to be used as a medicine. The purity of the compound can be tested by high-performance liquid chromatography and other appropriate methods known in the art. The compound should also be completely characterized using IR, UV and nuclear magnetic resonance spectroscopy.

As used herein, an effective amount of the colon tumor-inhibiting or tumor-reducing camptothecin compounds described above is intended to mean that amount of the compound which will inhibit the growth of or retard colon or colo-rectal cancer or malignant cells, kill malignant colon or colo-rectal cells, and cause the regression and palliation of malignant colon or colo-rectal tumors, i.e., reduce the volume or size of such tumors or eliminate the tumor entirely. These effective amounts comprise from about 2 to about 35 mg/kg, preferably from about 4 to about 15 mg/kg, and more preferably, from about 8 to about 13 mg/kg body weight. These effective amounts can be administered in daily treatments, or subdivided in a regimen of fewer treatments, for example, two administrations per week. It has been found according to the present invention that subdivided administrations in mammals, given two times per week, for as long as 5 to 6 weeks or longer, produce favorable therapeutic results with little or no toxicity.

With mammals, including humans, the effective amounts are preferably administered on the basis of body surface area. The interrelationship of dosages for animals of various sizes, species and humans (based on mg/$M^2$ of body surface) is described by Freireich, E. J., et al., *Cancer Chemother. Rep.*, 50(4):219 (1966). Body surface area may be approximately determined from the height and weight of an individual (see, e.g., Scientific Tables, Geigy Pharmaceuticals, Ardley, N.Y. pp. 537-538 (1970). An effective amount of the camptothecin compounds in the present invention can range from about 80 mg/$M^2$ of body surface per day to about 500 mg/$M^2$ of body surface per day.

Without wishing to be bound by any particular theory, it is believed that the camptothecin compounds that are useful in the present invention act to inhibit or retard malignant colon and colo-rectal tumors in mammals by inhibiting the activity of DNA topoisomerase I enzyme. This enzyme is linked to growth of malignant colon and colo-rectal tumors. The tumor-inhibiting or tumor-reducing camptothecin compounds of the invention are believed to interfere with DNA breakage-reunion facilitated by DNA topoisomerase I in these cells, by reversibly trapping the enzyme-DNA "cleavable complex" intermediate, thus interfering with DNA replication in the cell and, perhaps, with other vital functions.

It has now been recognized, as a part of this discovery, that the level (i.e., number of copies per cell) of DNA topoisomerase I was highly elevated in surgical specimens of colon malignant cells or malignant tumors, in comparison to the levels in the normal mucosa of the colon. Usually the enzyme is present at levels of less than $10 \times 10^5$ copies/cell, but in most specimens of colon cancerous or malignant tissue, the level of DNA topoisomerase is from about $10 \times 10^5$ to about $15 \times 10^6$ copies/cell. As part of the present invention, it was also recognized that the level of DNA topoisomerase I was highly elevated in human colon cancer xenografts, which were serially transplanted into immunodeficient, i.e., "nude" mice. The predictive value of the xenograft model has been described (see Giovanella et al., supra).

In particular, as described in the examples which follow, the enzyme levels of DNA topoisomerase I was found to be significantly elevated (above levels in normal colon mucosa) in malignant human colon tumors, e.g., cancers stage C1-C3, and C1-C3,D (advanced cancer with lymph node involvement and/or metastases) according to a staging classification (Astler, V. B. and Coller, F. C., *Am. Surg.*, 139:846, 1964.

The colon tumor-inhibiting or tumor-reducing camptothecin compounds of this invention may be administered in combination with pharmaceutically acceptable carriers or diluents, such as Tween/NaCl, e.g., Tween 80:0.15 NaCl,. Crempahor EL (D-12, NIH), Itralipid 10 or 20%, or other suitable emulsifiers for lipophilic compounds, and water-based solvents for the water-soluble compound, such as normal saline or phosphate buffered saline solutions.

In treating or retarding malignant colon and colo-rectal tumors in mammals in accordance with the present invention, the aforedescribed camptothecin compounds may be administered parenterally including subcutaneously, intraperitoneally, intramuscularly and intravenously. These camptothecin compounds may also be administered orally in suitable oral dosage forms to be described below. The preferred route of administration is intramuscular (lipophilic compounds) or IV (water-soluble compounds).

The present invention provides a pharmaceutical formulation comprising an effective amount for inhibiting the growth of a colon tumor of a colon tumor-inhibiting camptothecin compound, said compound being a member selected from the group consisting of 9-amino-20(RS-camptothecin, 10,11-methylenedioxy-20(RS)-camptothecin and the sodium salt of 10,11-methylenedioxy-20(RS)-camptothecin, or a combination thereof. Preferred is 9-amino-20(RS)-camptothecin. The pharmaceutical formulation may be administered via the parenteral route, including subcutaneously, intraperitoneally, intramuscularly and intravenously, as discussed above. The formulation can also be administered orally, intranasally or by transdermal patch in pharmaceutical compositions prepared by well-known methods. Examples of parenteral dosage forms include aqueous solutions of the active agent (i.e., colon tumor-inhibiting camptothecin compound) in isotonic saline, 5% glucose or other well known pharmaceutically acceptable liquids. The pharmaceutical compositions can be formulated in suitable oral dosage forms for oral administration. The active ingredient is contained in an ampoule with the lyophilized form and the emulsifier in separate vials to be formulated before the application or in a capsule (in liquid form) or a tablet. The quantity of effective dose, that is, the effective amount, supplied by each capsule or tablet is relatively unimportant since the total dosage can be reached by administration of either one or a plurality of capsules or tablets or both. Tablets or capsules may contain between 100 mg and 500 mg of the active camptothecin agent together with acceptable pharmaceutical excipients. The capsules employed may comprise any well known pharmaceutically acceptable material such as gelatin, cellulose derivatives, etc. Each capsule contains an appropriate amount of the biologically active agent (i.e., tumor-inhibiting camptothecin compound) dissolved in a suitable solvent comprising, e.g., polyethylene glycol USP, ethylene glycol USP, ethyl alcohol USP, purified water USP and mixtures thereof. The tablets may be formulated in accordance with conventional procedure employing solid carriers, lubricants, etc., well known in the art. Examples of solid carries are: starch, sugar, bentonite and other commonly used carriers. The biological agent of the present invention can also be dried and administered in the form of a hard shell tablet or a capsule containing, for instance, lactose or mannitol as a binder and conventional fillers and tabletting agents.

The camptothecin compounds of the invention may be administered to patients afflicted with malignant lesions of the colon as part of a treatment regimen to effectively inhibit or kill or retard malignant cells of colonic and colo-rectal tumors, to inhibit the DNA topoisomerase I enzymatic activity therewith, to reduce the size of malignant colon and colo-rectal tumors, thereby treating the malignant human colon and colo-rectal tumor. The colon lesions that may be treated with the present invention may .be located in the colonic mucosa, or elsewhere in the bowel wall, or in the serosa and mesenteric fat or, in the liver, and other organs or tissues, and may be of the poorly differentiated, moderately differentiated, well differentiated variety (on microscopic examination). The frequency and duration of treatment with the compounds of the invention will vary widely from patient to patient, depending on the severity and stage of the patient's colon cancer disease and on the severity and toxic side-effects. Merely by way of example, the camptothecin compounds may be administered 1 to 2 times per week for a period of time up to 6–10 weeks or longer.

Another important feature of the method provided by the present invention relates to the relatively low or no apparent overall toxicity of the camptothecin compounds administered in accordance herein. Overall toxicity can be judged using various criteria. For example, loss of body weight in a subject over 10% of the initially recorded body weight (i.e., before treatment) can be considered as one sign of toxicity. In addition, loss of overall mobility and activity and signs of diarrhea or cystitis in a subject can also be interpreted as evidence of toxicity. In one of the examples which follow, the overall toxicity of the camptothecin compounds was evaluated. For example 9-amino-20(RS)-camptothecin and 10,11-methylene dioxy-20(RS)-camptothecin, when administered two times per week in amounts of 150 and 100 mg/kg, respectively, were found to be therapeutically effective (resulting in complete reduction of subcutaneous tumors) with no overall toxicity as described above.

The working examples set forth below are intended to illustrate the invention without limiting its scope.

EXAMPLE 1

Determination of DNA Topoisomerase I Activity Levels

DNA topoisomerase I levels in surgical specimens of normal human mucosa of the colon, primary adenocarcinoma of the colon, and in human colon cancer xenografts were determined as follows:

The topoisomerase enzyme was purified to homogeneity from HeLa cells, and the preparation of antisera to the enzyme followed an established procedure. Liu L. F., et al. *Proc. Natl. Acad. Sci. U.S.A.* 78:3487 (1981); and Haligan, B. D., et al., *J. Biol. Chem.* 260:24–75 (1985). Under the supervision of a pathologist, tissues of colonic tumors and of normal mucosa were frozen in liquid nitrogen within one hour after the surgery, and stored in multiple aliquots at $-80°$ C. for further analysis. Specimens were also obtained from four lines of colon-cancer xenografts, growing 10–13 days in NCI-1 immunodeficient mice (Charles River Breeding, Wilmington, Mass). The immunoblot analysis for topoisomerase I was performed as described previously. Hsiang, Y-H., et al., *Cancer Res.* 49:4385 (1989). DNA content of tissue homogenates was estimated using an established procedure as described in this publication, ibid. DNA content was used for the normalization of enzyme levels, which were expressed as number of copies per cell.

The results of Example 1 (illustrated in FIG. 1) indicate that DNA topoisomerase I was present in high levels in most colon cancer specimens. The circles in FIG. 1 show topoisomerase I levels in individual specimens and the histograms indicate the means (average of several trials) of topoisomerase I copies per cell. The enzyme levels are significantly elevated (above levels in normal colon mucosa) in cancers stage C1–C3, and C1–C3,D (advanced cancer with lymph node involvement and/or metastases; ($P<0.01$; t-test with Bonferroni correction). Astler, V. B., et al., *Ann. Surg.* 139:846 (1964). These results show that most specimens of human colon cancer have an abundance of topoisomerase I.

EXAMPLES 2–5

In vivo Administration of Colon-Cancer Inhibiting Compounds

In these four examples, three xenograft lines of human colon cancer were selected to test the effectiveness of various drugs or compounds in treating human colon cancer. These xenograft lines included the following: (1) A moderate-to-poorly differentiated human colon cancer HT-29; (2) poorly differentiated colon cancer lines designated CASE; and (3) SW48. Liebowitz, A. et al., *Cancer Res.* 36:4562 (1976); and Fogh, J., et al., *Human Tumor Cells In Vivo*, J. Fogh, ed. Plenum Press, New York, pp. 115–159 (1975). The HT-29, CASE and SW48 cell lines were implanted into immunodeficient NIH-1 mice. Each control or drug-treated group included 6 males. Tumor fragments were implanted on day 0. For each implant, 50 mg of wet weight finely minced tumor tissue in 0.5 ml EMEM (Gibco, Grand Island, N.Y.) was injected under the skin over the right dorsal chest region. The drugs were formulated in Tween 80:0.15 NaCl and injected subcutaneously, with the exception of doxorubicin, which was injected intravenously. The treatment started on day 7 and continued 2x/week for 5–6 weeks. Drug doses were based on an established median toxic dose for the schedule applied. Controls were treated with the solvent only. The tumors were measured in three dimensions with a caliper, and tumor volume calculated. The care and treatment of experimental mice was in accordance with institutional guidelines.

Figure 2:
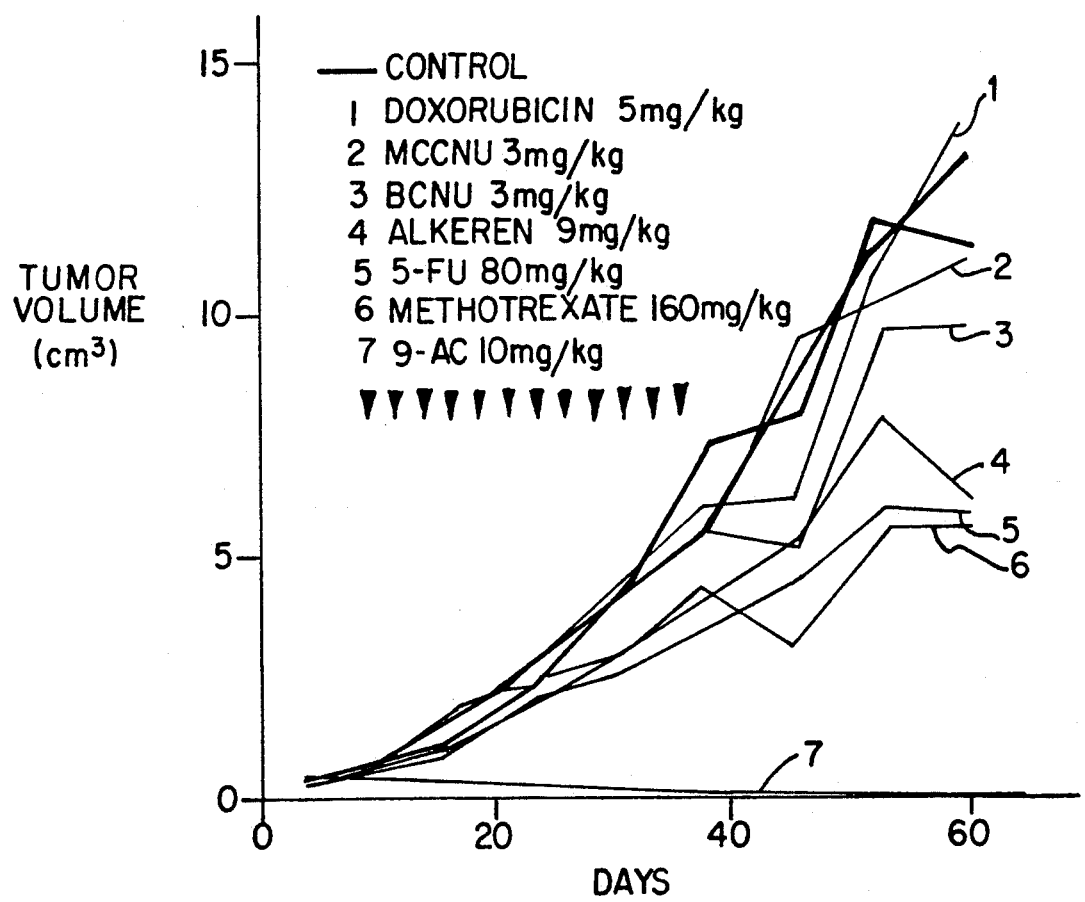
FIG. 2 depicts the results obtained by treating immunodeficient or "nude" mice into which HT-29 human colon cancer cell lines had been transplanted (i.e., xenografts), with 9-amino-20(RS)-camptothecin of the present invention.

The results of Example 2 using the HT-29 cell lines are shown in FIG. 2. In FIG. 2, 9-AC represents 9-amino-20(RS)-camptothecin. The means of tumor volumes in cubic centimeters ($cm^3$) were plotted against time; S.D. (standard deviation) of the means was less than 15% of the value.

Among the nine anti-tumor agents tested, only marginal growth-retardation of tumor implants was noticed in some cases (e.g., 5-fluorouracil, 80 mg/kg of body weight/dose or methotrexate, 160 mg/kg body weight/dose). Mice treated with camptothecin derivatives showed marked inhibition of tumor growth. Five out of six (5/6) mice with HT-29 tumors, injected subcutaneously twice a week with 9-amino-20(RS) 10 mg/kg body weight/dose, for a total of 6 weeks, showed no evidence of disease (NED) or minimal disease (tumor volume=0.1 $cm^3$) (see FIG. 2). In another group, 6/6 mice treated with 12.5 mg/kg body weight/dose had NED or minimal disease. The remission lasted (means+S.D.) 62±20 and 56±15 days, respectively. The appearance of a palpable nodule followed by continuous tumor regrowth signaled the end of a remission.

Figure 3:
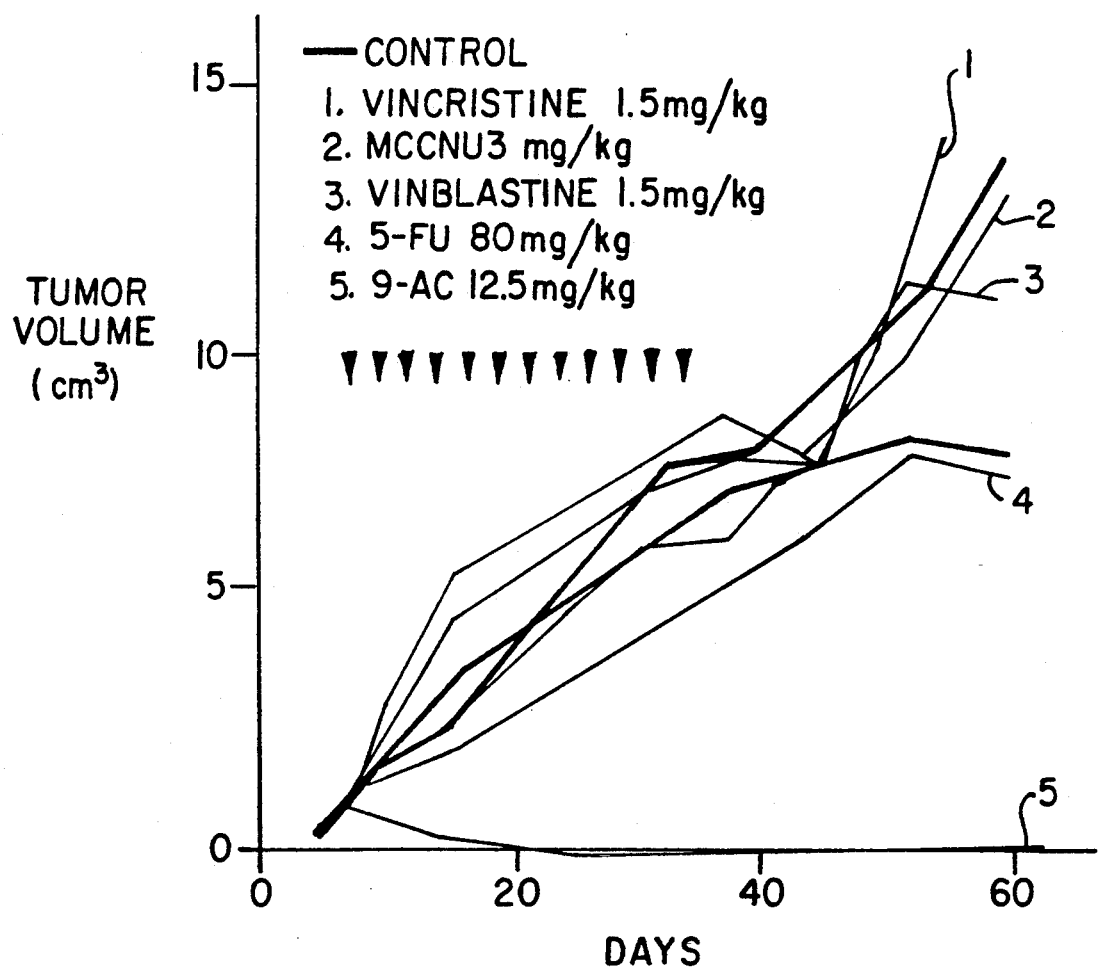
FIG. 3 shows the results obtained by treating mice afflicted with a poorly differentiated human colon cancer cell line designated CASE with anti-tumor agents including 9-amino-20(RS)-camptothecin.

In Example 3, the CASE cell line was employed. The results of Example 3 after the first course of treatment using the CASE cell line are shown in FIG. 3. These results demonstrate that the first course of treatment (12.5 mg/kg body weight) with 9-amino-20(RS)-camptothecin had induced NED or minimal disease in 6/6 mice transplanted with the CASE cell line.

Figure 4:
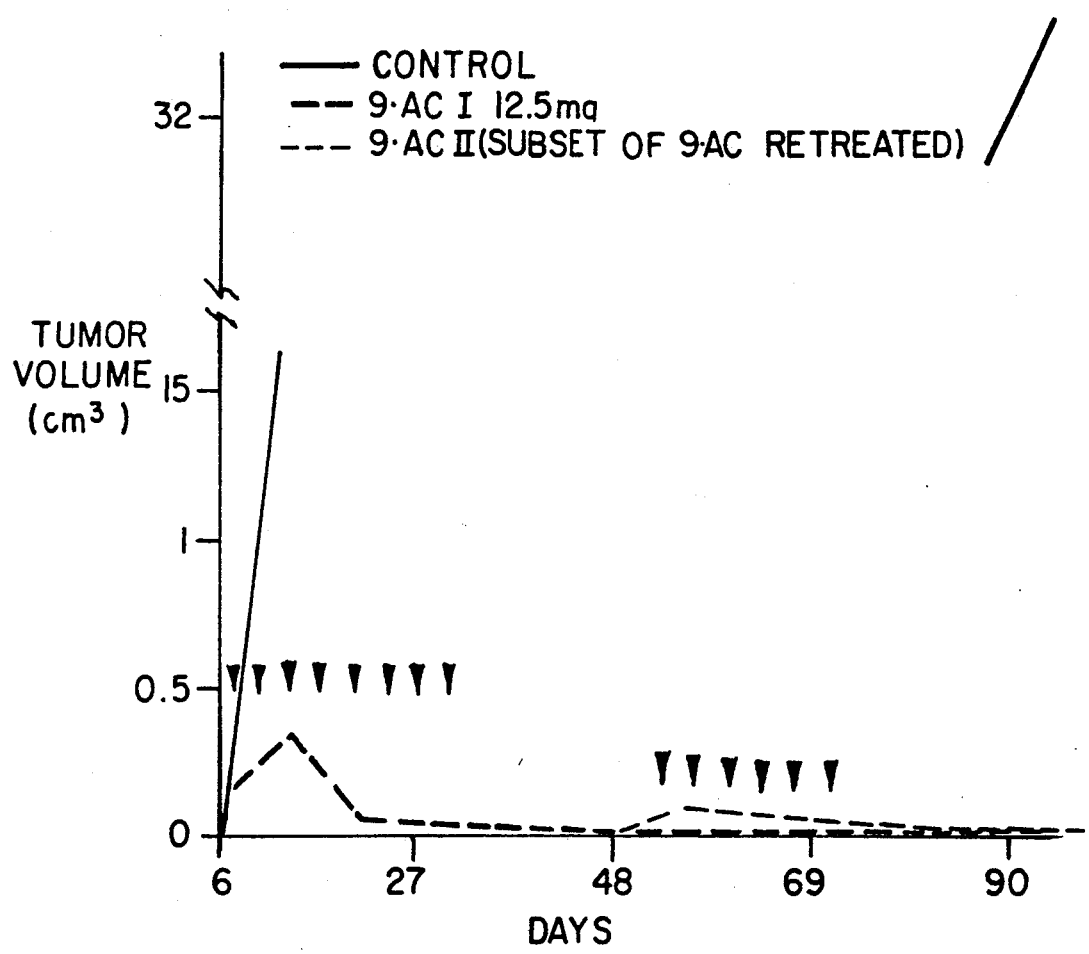
FIG. 4 shows the results of the treatment obtained in the CASE cell line using 9-amino-20(RS)-camptothecin after a first course of treatment (12.5 mg/kg body weight/dose) and a second course of treatment with the same dose (75 mg/kg body weight total dose).

Example 4 illustrates the results of an experiment in which a second course of treatment followed a first course of treatment. The results of Example 4 are shown in FIG. 4. On day 51 after tumor implantation, mice with CASE tumors and minimal disease received the second course of therapy. These mice received a total of 14 injections (doses) of 12.5 mg/kg body weight/dose (FIG. 4). It was observed that 5/6 mice had NED and the other had minimal disease. A long-term tumor-free survival (in excess of 7 months) was observed in 7/8 treated mice with CASE tumors.

In Example 5, a course of treatment was carried out with the SW48 human colon cancer cell line. This tumor line is extremely unresponsive to treatment. Liebowitz, A., et al., *Cancer Res.* 36:4562 (1976); and Fogh, J., et al., *Human Tumor Cells in Vitro*, J. Fogh, ed. Plenum Press, New York, pp. 115-159 (1975).

From FIG. 5, it can be seen that the first course of treatment of (12.5 mg/kg body weight) induced NED or minimal disease in 6/6 mice.

It can also be seen in FIG. 5 that following the first course of treatment, the second course of treatment (75 mg/kg body weight total dose) was also administered to mice with SW48 tumors and minimal disease. A long-term tumor-free survival (in excess of 7 months) was observed in 6/6 mice with SW48 tumors.

It should be noted that the first course of treatments of the CASE and SW48 lines, described above, started with well-established tumors, averaging 0.2-0.25 cm$^3$ in volume. In Example 5, day=35 SW48 tumors (average size 2.5 cm$^3$), were selected for the first treatment with 9-amino-20(RS)-camptothecin. The disparity of tumor-sizes between the control and treated groups is intentional (see FIG. 5): The largest tumors available were selected for treatment with 6 doses of 9-amino-20(RS)-camptothecin (12.5 mg/kg body weight/dose, delivered twice a week). There was a notable 91% reduction (on average) in the volume of the tumors in treated mice. A second course of treatment of the HT-29 line was administered to mice with an average tumor size of 8.3 cm$^3$. A total dose of 60 mg/kg body weight of 9-amino-20(RS)-camptothecin reduced the tumor volume by 45% on average.

EXAMPLE 6

In vivo Efficiency of 10,11-Methylenedioxy-20(RS) camptothecin Sodium Salt 10,11-methylenedioxy-20(RS)-camptothecin and its sodium (Na+) salt, a water-soluble compound, are highly active in topoisomerase I-directed screens and was selected for in vivo tests. Daily injections or 2 injections per week of 10,11-methylenedioxy-20(RS)-camptothecin (total doses 50-70 mg/kg of body weight) stopped the growth of day-7 CASE tumors for a period of 4-6 weeks in 6/6 mice. Five injections of 10,11-methylenedioxy-20(RS)-camptothecin sodium salt (10 mg/kg body weight/dose) stopped the growth of day-7 CASE tumors in 6/6 mice for a period of 4 weeks. Both drugs inhibited at 30 mg/kg body weight (total dose) the growth of metastases of human colon cancer in the liver of immunodeficient mice, and increased the survival of such mice by ~100% (from average of 23 to 46 days).

EXAMPLE 7

Evaluation of Toxicity

The overall toxicity of the colon tumor-inhibiting camptothecin compounds was next to be evaluated at various dosages. The overall toxicity of 9-amino-20(RS)-camptothecin, 10,11-methylenedioxy-camptothecin and the sodium salt of 10,11-methylenedioxy-camptothecin was evaluated in this example as follows: tumor fragments were implanted under the skin of 5-6 mice in each group beginning on day 0. The mice were injected with one of the compounds beginning on day 7 after visible signs that malignant growth of the implanted tumor had occurred. The injections of the compound were given at predetermined doses of 10 or 12.5 mg/kg of body weight per week for a total of 3-6 weeks. Injections were daily or given two times per week. The body weights of the controls (mice with tumors, injected with placebo) and that of the drug-treated mice were taken two times each week and recorded. Overall toxicity was determined in the following way: loss of body weight after treatment in a subject of more than 10% over the initial body weight of the subject recorded at the beginning of the experiment, was considered a sign of toxicity. The mice were also monitored for their ability to regain the lost body weight. Regaining entirely its lost body weight would therefore be a sign of low toxicity in a subject. In addition, mice were monitored for their overall mobility and activity as well as for signs of diarrhea or cystitis. Mobility/activity was judged on a sliding scale of 1 to 5. That is, a score of 1 indicated good mobility/activity and a score of 5 indicated poor mobility/activity. Diarrhea and cystitis were judged on a plus/minus basis.

The results of the toxicity evaluation are set forth in Table 1 below.

TABLE 1

| Drug | Total Dose | Overall Toxicity | Therapeutic Responses |
|---|---|---|---|
| Toxicity-Daily Treatment | | | |
| 10,11-Methylene-dioxy-20(RS) Na+ | 25 mg/kg | animal deaths | PR* |
| 10,11-Methylene-dioxy-20(RS) Na+ | 25 mg/kg | body weight loss < 10% | PR |
| 10,11-Methylene-dioxy-20(RS) Na+ | 200 mg/kg | animal deaths | PR |
| Toxicity-Twice/Week Treatment | | | |
| 20(S)-Camptothecin | 70 mg/kg | animal deaths | PR |
| 20(S)-Camptothecin | 50 mg/kg | animal deaths | PR |
| 20(S)-Camptothecin | 28 mg/kg | body weight loss > 15% | PR |
| 10,11-Methylene-dioxy-20(RS) Na+ | 50 mg/kg | body weight loss 20% | CR** |
| 10,11-Methylene-dioxy-20(RS) Na+ | 62.5 mg/kg | animal deaths | PR |
| 10,11-Methylene-dioxy-20(RS) | 100 mg/kg | none | CR |
| 10-Amino-20(RS)-camptothecin | 100 mg/kg | body weight loss < 15% | PR |
| 9-Amino-20(RS)-camptothecin | 150 mg/kg | none | CR |
| 9-Amino-20(RS)-camptothecin | 175 mg/kg (cumulative) | body weight loss ≦ 20% | CR |

*PR, partial reduction of subcutaneous tumors.
**CR, complete reduction of subcutaneous tumors.

The results in Table 1 indicate that the camptothecin compounds when administered in accordance with the method provided by this invention, unexpectedly exhibited little or no overall toxicity at all. Even at high doses, camptothecin compounds, such as 9-amino-20(RS)-camptothecin (150 mg/kg total dose; 2 times per week) and 10,11-methylenedioxy-20(RS) camptothecin (100 mg/kg total dose; 2 times per week) exhibited no overall toxicity while at the same time providing an excellent therapeutic response by completely reducing subcutaneous tumors in the subjects.

It is noteworthy that the response of treated animals would have allowed either higher doses or a treatment course delivered over a longer time period, i.e., longer duration. While 50 mg/kg body weight of 20(S)-camptothecin, 25 mg/kg body weight of 10-amino-20(RS)-camptothecin, and 62.5 mg/kg body weight of 10,11-methylenedioxy-20(RS)-camptothecin Na+ salt led to toxic deaths of all animals, 50 mg/kg body weight of 10,11-methylenedioxy-20(RS) Na+ salt resulted in only 26% body weight loss followed by rapid recovery and gains in body weight, and 70 mg/kg body weight (total dose) of 10,11-methylenedioxy-20(RS)-camptothecin decreased the body weight by less than 10%.

The second course of treatment with 50–75 mg/kg body weight of 9-amino-20(RS)-camptothecin appears to be more toxic than the first. The body weight dropped by 19% on the average (CASE and SW48 tumor lines) but again recovered rapidly. The poorer performance of mice receiving the second course of treatment may be explained by a cumulative toxicity of the two treatments. There were no signs of gastrointestinal toxicity or sterile hemorrhagic cystitis, which had been observed among patients treated with 20(S)-camptothecin Na+ Salt. Gottlieb, J. A., et al., supra.; and Muggia F. M., et al., supra.

What is claimed is:

1. A method of treating malignant colon tumors in a mammal in need of such treatment which comprises administering to said mammal an effective amount for treating said tumor of a tumor inhibiting camptothecin compound selected from the group consisting of 9-amino-20(RS)-camptothecin, 10,11-methylenedioxy-20(RS)-camptothecin and the sodium salt of 10,11-methylenedioxy-20(RS)-camptothecin, or a combination thereof.

2. The method according to claim 1 wherein said colon tumors comprise colo-rectal tumors.

3. The method according to claim 1 wherein said tumor inhibiting camptothecin compound comprises 9-amino-20(RS)-camptothecin.

4. The method according to claim 1 wherein said tumor inhibiting camptothecin compound comprises 10,11-methylenedioxy-20(RS)-camptothecin.

5. The method according to claim 1 wherein said tumor inhibiting compound comprises the sodium salt of 10,11-methylenedioxy-20(RS)-camptothecin.

6. The method according to claim 1 wherein said effective amount comprises from about 2 mg/per kg of body weight per week to about 35 mg/per kg of body weight per week.

7. The method according to claim 6 which comprises dividing said effective amount into doses to be administered more than once a week but wherein the total dosage administered per week is from about 2 mg/per kg of body weight to about 35 mg/per kg of body weight.

8. The method according to claim 6 which comprises administering said effective amount in divided doses about two times per week.

9. The method according to claim 1 which comprises parenteral administering said tumor inhibiting camptothecin compound said mammal.

10. The method according to claim 9 wherein said parenteral administration of the tumor inhibiting camptothecin compound comprises subcutaneous injection.

11. A method for retarding a colo-rectal tumor in a mammal in need of such treatment which comprises administering to said mammal an effective amount for retarding said tumor of a colo-rectal inhibiting camptothecin compound.

12. A pharmaceutical formulation comprising an effective amount for inhibiting the growth of a colon tumor of a colon tumor-inhibiting camptothecin compound selected from the group consisting of 9-amino-20(RS)-camptothecin, 10,11-methylenedioxy-20(RS)-camptothecin and the sodium salt of 10,11-methylenedioxy-20(RS)-camptothecin, or a combination thereof.

13. The pharmaceutical formulation according to claim 12 wherein said compound comprises 9-amino-20(RS)-camptothecin.

14. The pharmaceutical formulation according to claim 12 comprising from about 100 mg to about 500 mg of said camptothecin compound.

15. The pharmaceutical formulation according to claim 12 comprising a parenteral dosage form.

16. The pharmaceutical formulation according to claim 12 comprising an oral dosage form selected from the group consisting of a tablet and a capsule.

17. A method of treating malignant colon tumors in a mammal in need of such treatment which comprises administering to said mammal an effective amount for treating said tumor of a tumor inhibiting camptothecin compound selected from the group consisting of 9-amino-20(S)-camptothecin, 10,11-methylenedioxy-20(S)-camptothecin and the sodium salt of 10,11-methylenedioxy-20(S)-camptothecin, or a combination thereof.

18. The method according to claim 17 wherein said colon tumors comprise colo-rectal tumors.

19. The method according to claim 17 wherein said tumor inhibiting camptothecin compound comprises 9-amino-20(S)-camptothecin.

20. The method according to claim 17 wherein said tumor inhibiting camptothecin compound comprises 10,11-methylenedioxy-20(S)-camptothecin.

21. The method according to claim 17 wherein said tumor inhibiting compound comprises the sodium salt of 10,11-methylenedioxy-20(S)-camptothecin.

22. The method according to claim 17 wherein said effective amount comprises from about 2 mg/per kg of body weight per week to about 35 mg/per kg of body weight per week.

23. The method according to claim 22 which comprises dividing said effective amount into doses to be administered more than once a week but wherein the total dosage administered per week is from about 2 mg/per kg of body weight to about 35 mg/per kg of body weight.

24. The method according to claim 22 which comprises administering said effective amount in divided doses two times per week.

25. The method according to claim 17 which comprises parenterally administering said tumor inhibiting camptothecin compound to said mammal.

26. The method according to claim 25 wherein said parenteral administration comprises subcutaneous injection.

27. A pharmaceutical formulation comprises an effective amount for inhibiting the growth of a colon tumor of a colon tumor-inhibiting camptothecin compound selected from the group consisting of 9-amino-20(S)-camptothecin, 10,11-methylenedioxy-20(S)-camptothecin and the sodium salt of 10,11-methylenedioxy-20(S)-camptothecin, or a combination thereof.

28. The pharmaceutical formulation according to claim 27 wherein said compound comprises 9-amino-20(S)-camptothecin.

29. The pharmaceutical formulation according to claim 27 comprising from about 100 mg to about 500 mg of said camptothecin compound.

30. The pharmaceutical formulation according to claim 27 comprising a parenteral dosage form.

31. The pharmaceutical formulation according to claim 27 comprising an oral dosage form selected from the group consisting of a tablet and a capsule.

* * * * *